United States Patent [19]  [11] Patent Number: 5,053,395
Nishio et al.  [45] Date of Patent: Oct. 1, 1991

[54] PRADIMICIN AMIDE DERIVATIVES

[75] Inventors: Maki Nishio; Seiji Iimura, both of Tokyo; Toshikazu Oki, Yokohama, all of Japan

[73] Assignee: Bristol-Myers Company, New York, N.Y.

[21] Appl. No.: 328,201

[22] Filed: Mar. 24, 1989

[51] Int. Cl.$^5$ .................. A61K 31/70; C07H 15/24
[52] U.S. Cl. .................. 514/33; 536/16.8; 536/17.9; 536/18.1
[58] Field of Search .............. 536/6.4, 18.1, 17.9, 536/16.8; 514/27, 33; 562/553

[56] References Cited

U.S. PATENT DOCUMENTS 4,870,165 9/1989 Oki et al. .................. 536/6.4

FOREIGN PATENT DOCUMENTS 277621 8/1988 European Pat. Off. .

OTHER PUBLICATIONS

J. Antibiotics, 1988, 41:807–811.
J. Antibiotics, 1988, 41:1019-28.
Abstract No. 984 of 27th Interscience Conf. on Antimicrobial Agents and Chemotherapy (NY, N.Y., Oct. 4-7, 1987).

*Primary Examiner*—Elli Peselev
*Attorney, Agent, or Firm*—Mollie M. Yang

[57] ABSTRACT

Disclosed herein are pradimicin amides which are active as antifungel agents.

14 Claims, No Drawings

PRADIMICIN AMIDE DERIVATIVES

BACKGROUND OF THE INVENTION

The present invention relates to pradimicin amides which are active as antifungal agents, to pharmaceutical compositions containing them, and to their use for treating fungal infections.

Few examples of benzo[a]naphthacene quinones derived from microbial sources have been reported and these include compounds designated G-2N and G-2A, and KS-619-1. While no biological activity was reported for G-2N and G-2A, KS-619-1 was disclosed as inhibitor of calcium ion and calmodulin-dependent cyclic nucleotide phosphodiesterase. Recently, published European Patent Application 277,621 discloses antifungal antibiotics BU-3608 (Ia), BU-3608 B (Ib), and BU-3608 C (Ic). Antibiotics benanomicins A and B were reported in J. Antibiotics, 1988, 41:807–811; benanomicin B appears to be the same as BU-3608 C whereas benanomicin A has a hydroxyl group in place of the sugar amino group.

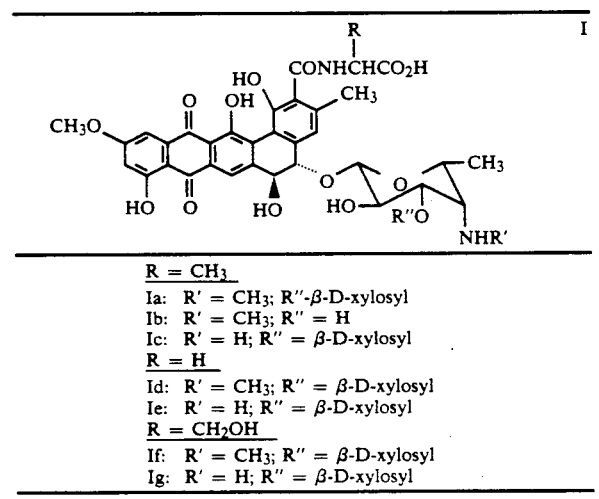

R = CH₃
- Ia: R' = CH₃; R''-β-D-xylosyl
- Ib: R' = CH₃; R'' = H
- Ic: R' = H; R'' = β-D-xylosyl R = H
- Id: R' = CH₃; R'' = β-D-xylosyl
- Ie: R' = H; R'' = β-D-xylosyl R = CH₂OH
- If: R' = CH₃; R'' = β-D-xylosyl
- Ig: R' = H; R'' = β-D-xylosyl Our co-pending U.S. application Ser. No. 203,776, filed June 7, 1988 discloses BU-3608 D (Id) and BU-3608 E (Ie). BU-3608 FA-1 (If) and FA-2 (Ig) and derivatives thereof are disclosed in our co-pending U.S. application Ser. No. 269,821 filed Nov. 10, 1988. N-alkylated derivatives of the BU-3608 group of compounds are disclosed in our co-pending U.S. application Ser. No. 221,144 filed July 19, 1988.

SUMMARY OF THE INVENTION

The present invention provides compounds of formula II

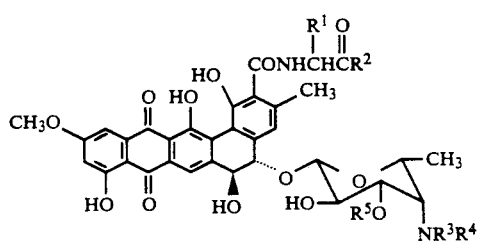

wherein $R^1$ is selected from the group consisting of H, methyl and hydroxymethyl, and when $R^1$ is methyl or hydroxymethyl the resulting amino acid residue has the D-configuration; $R^2$ is selected from the group consisting of $-NR^6R^7$, $-NHNR^6R^7$, $-NHCH_2CO_2H$ and (D)—$NHCH(CH_3)CO_2H$; $R^6$ is H and $R^7$ is selected from the group consisting of H, $C_{1-6}$alkyl, $C_{3-6}$cycloalkyl, $C_{6-10}$aryl and $C_{7-15}$aralkyl; or $R^6$ and $R^7$ are independently $C_{1-6}$alkyl; or $R^6$, $R^7$ and the nitrogen to which they are attached form a 3- to 6-membered ring; $R^3$ and $R^4$ are each independently selected from the group consisting of H and $C_{1-6}$alkyl; and $R^5$ is H or β-D-xylosyl; or a pharmaceutically acceptable salt thereof.

There is provided by a further aspect of the present invention pharmaceutical compositions for treatment of fungal infections comprising an antifungal effective amount of a compound of Formula II and a pharmaceutically acceptable carrier.

A further aspect of the present invention provides a method for treatment of fungal infections in a mammalian host comprising administering to said infected host an antifungal effective amount of a compound of Formula II.

DETAILED DESCRIPTION OF THE INVENTION

Pradimicin A refers to the antifungal agent formerly known as BU-3608; BU-3608 B, C, D, and E is now pradimicin B, C, D, and E, respectively. As used herein, the term "alkyl" includes both straight and branched alkyl chains; "pharmaceutically acceptable salt" includes acid addition salts formed with, for example, hydrochloric acid, hydrobromic acid, sulfuric acid, phosphoric acid, nitric acid, acetic acid, tartaric acid, citric acid, methansulfonic acid, succinic acid and the like; base salts with an alkali metal base such as sodium or potassium hydroxide, carbonate, and bicarbonate; and when possible, internal salt.

In a preferred embodiment of compounds of Formula II, $R^2$ is selected from the group consisting of amino, $C_{1-6}$alkylamino, di($C_{1-6}$)alkylamino, hydrazino, glycyl and D-alanyl. Alkyl is more preferably of from one to four carbon atoms.

In another preferred embodiment of compounds of Formula II, $R^1$ is methyl.

In yet another preferred embodiment of compounds of formula II, $R^3$ is H and $R^4$ is H or methyl, or $R^3$ and $R^4$ are both methyl; more preferably $R^3$ is H and $R^4$ is methyl.

Compounds of the present invention are prepared by reacting a pradimicin of formula

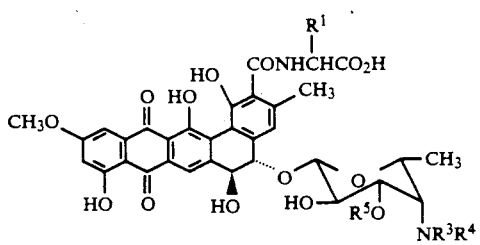

wherein $R^1$ is H, methyl or hydroxymethyl; $R^3$ and $R^4$ are independently selected from the group consisting of H and $C_{1-6}$alkyl; and $R^5$ is H or β-D-xylosyl; or an acylating equivalent thereof with an appropriate amine.

The amine reactant may be ammonia, primary amine, secondary amine, hydrazine, mono- or disubstituted hydrazine, or an amino acid. Examples of suitable amines include, but are not limited to, ammonia, methylamine, ethylamine, propylamine, isopropylamine, butylamine, pentylamine, hexylamine, dimethylamine, ethylmethylamine, phenylamine, benzylamine, phenethylamine, cyclobutylamine, cyclohexylamine, piperidine, pyrrolidine, hydrazine, methylhydrazine, 1,1-dimethylhydrazine, glycine, and D-alanine. Where the amine is an amino acid, the non-reacting functional groups, e.g. the carboxyl group, are preferably protected. Suitable carboxyl protecting groups are for example lower alkyl esters, benzyl and benzhydryl esters and t-butyl esters.

The starting material pradimicins A, B and C are produced by fermentation of Actinomadura hibisca strains P157-2 (ATCC 53557) and Q278-4 (ATCC 53646) as disclosed in our co-pending U.S. application Ser. No. 115,273 filed Nov. 2, 1987; the production of pradimicins D and E by the mutant strain A2660 (ATCC 53762) derived from the parent strain P157-2 is disclosed in U.S. Ser. No. 203,776 filed June 7, 1988; and the production of pradimicins FA-1 and FA-2 by mutant strains A2493 (ATCC 53815) and B0012 (ATCC 53816) capable of incorporating supplemented D-serine and derived from the parent strain P157-2 is disclosed in U.S. Ser. No. 269,821 filed Nov. 10, 1988. The general procedure for alkylating the sugar amino group via reductive alkylation is provided in U.S. Ser. No. 221,144, filed July 19, 1988. The preparation of desxylosyl pradimicins by acid hydrolysis is provided in the specification of the above-mentioned applications. The disclosure of each of the above-mentioned applications is hereby incorporated by reference.

The acylating species may be the carboxylic acid of the pradimicin component or it may be a reactive derivative thereof, for example an acid halide, an active ester or a mixed anhydride. The acid halide may be generated by reacting the carboxylic acid with a halogenating agent such as thionyl chloride, phosphorous trichloride, phosphorous pentachloride and oxalyl chloride in the presence of a tertiary amine base to neutralize the acid produced. Active esters may be prepared by reacting the carboxylic acid with an alcohol such as a lower alkanol, an aromatic alcohol, benzyl alcohol or an N-hydroxy compound such as N-hydroxybenzotriazole and N-hydroxysuccinimide, in the presence of a catalytic amount of an acid such as sulfuric acid or toluenesulfonic acid or in the presence of a coupling agent dicyclohexylcarbodiimide (DCC). Mixed anhydrides may be obtained by treating the pradimicin with an acid chloride derived from for example alkanoic acids or aromatic carboxylic acids. When the pradimicin reactant is used in the free acid form, the coupling reaction is advantageously carried out in the presence of a condensing agent such as DCC.

The sugar amino group of the pradimicin reactant is optionally protected. Protection of the amino group is preferred when a coupling agent is used in conjuction with the free acid in the acylation step or when the acid chloride is employed. The protecting groups for the amino group are not particularly limited but may be any that can be put on and removed easily without adversely affecting the rest of the molecules. Suitable amino protecting groups include benzyloxycarbonyl, t-butoxycarbonyl, toluenesulfonyl, trifluoroacetyl and chloroacetyl; in our experience, the benzyloxycarbonyl (CBZ) group has served as a convenient amino protecting group. The selection of amino and/or carboxyl protecting groups, and methods of blocking and deblocking the non-reacting amino and/or carboxyl groups are discussed in monographs such as "Protective Groups in Organic Chemistry" J. F. W. McOmie, Plenum Press, 1973 and "Peptide Synthesis" M. Bodansky et al, Wiley, 1976, and are generally within the skills of one of ordinary skill in organic synthesis.

The condensation reaction is carried out in an organic solvent such as tetrahydrofuran, dimethylformamide, acetone, a lower alkanol, methylene chloride and acetonitrile, or an aqueous mixture thereof. The temperature at which the reaction is conducted is not particularly restricted and may range from 0° C. to 100° C. although room temperature is preferred. The reaction time needed depends on the particular reactants used and the temperature at which the reaction is carried out and may range from several minutes to several days.

After the completion of the reaction amino and/or carboxyl protecting groups are removed using conventional methods and the choice of deblocking method depends on the protecting groups used. For example, the CBZ group can be readily removed by catalytic hydrogenation, and ester of the D-amino acid moiety can be saponified to give the free carboxyl group. The desired product of the present invention may then be recovered and purified using standard techniques such as solvent partition, recrystallization, and column chromatography.

BIOLOGICAL PROPERTIES

Antifungal activities of representative compounds of the present invention were evaluated both in vitro and in vivo. The minimum inhibitory concentrations (MICs) against various fungi were determined by serial agar dilution method using Sabouraud dextrose agar. Thus, approximately 0.003 ml of fungal suspension containing $10^6$ cells/ml was applied to the surface of agar plates containing the test antibiotics. The MIC values recorded after the cultures had been incubated for 44 hours at 28° C. are set forth below in Table I.

TABLE I

| Compound of Example | In vitro Antifungal Activity MIC (μg/ml) | | | |
| --- | --- | --- | --- | --- |
| | C. albicans | C. neoformans | A. fumigatus | T. mentagrophytes |
| 1 | 25 | 6.3 | >100 | >100 |
| 2 | 12.5 | 1.6 | 6.3 | 12.5 |
| 3 | 50 | 3.1 | 25 | 25 |
| 4 | 6.3 | 1.6 | 6.3 | 12.5 |
| 5 | 6.3 | 1.6 | 6.3 | 6.3 |
| 6 | 100 | 3.1 | 50 | 100 |
| 7 | >50 | 12.5 | >50 | >50 |

In vivo activity of compounds of the present invention was tested against Candida albicans A9540 infection in mice. Test organisms were cultured for 18 hours at 28° C. in YGP medium (yeast extract, glucose, peptone, $K_2HPO_4$, $MgSO_4$) and then suspended in saline.

Male ICR mice weighing 20 to 24 g were infected intravenously with about 10 times the median lethal dose of the test fungus. The antibiotic at various dose levels was administered to groups of 5 mice each intravenously just after the fungal infection. The dose that protects 50% of the animals from infection ($PD_{50}$, mg/kg) was calculated from survival rates recorded on the 20th day after the fungal challenge. All control animals died within 7 to 15 days after infection. The $PD_{50}$ for compounds of Examples 2, 4, and 5 are 18 mg/kg, 11 mg/kg and 8.8 mg/kg, respectively.

Accordingly, another aspect of the present invention provides a method for treating fungal infections which comprises administering to a host infected with a susceptible fungus an antifungal effective amount of a compound of the present invention. For treatment of fungal infections in animals and human beings, the antibiotics of the present invention may be given in an antifungally effective amount by any accepted routes of administration; these include, but are not limited to, intravenous, intramuscular, oral, intranasal, and for superficial infections, topical administration. Preparations for parenteral administration include sterile aqueous or non-aqueous solutions, suspensions or emulsions. They may also be manufactured in the form of sterile solid compositions which can be dissolved in sterile water, physiological saline, or some other sterile injectable medium immediately before use. Oral formulation may be in the form of tablets, gelatin capsules, powders, lozenges, syrups, and the like. For topical administration, the compound may be incorporated into lotions, ointments, gels, creams, salves, tinctures, and the like. Unit dosage forms may be prepared using methods generally known to those skilled in the art of pharmaceutical formulations.

It will be appreciated that when treating a host infected with a fungus susceptible to the antibiotics of this invention, the actual preferred route of administration and dosage used will be at the discretion of the attending clinician skilled in the treatment of fungal or viral infections, and will vary according to the causative organism, its sensitivity to the antibiotic, severity and site of the infection, and patient characteristics such as age, body weight, rate of excretion, concurrent medications, and general physical condition.

The following examples serve to illustrate the present invention without limiting its scope which is solely defined by the claims appended to the end of the specification.

Preparation Of N-benzyloxycarbonyl Pradimicin A
(N-Cbz Pradimicin A)

Benzyl chloroformate (5 ml) was added dropwise to a solution of pradimicin A.HCl (2.5 g) and sodium carbonate (7.5 g) in 50% aqueous acetone (800 ml) at 0° C. The mixture was stirred for 1 hr at 0° C. and 3 hrs at 10° C. and then concentrated to 200 ml. The resulting solution was mixed with methanol (200 ml) and 6N sodium hydroxide (70 ml), and kept for 15 hrs at room temperature to deblock the O-benzyloxycarbonyl groups. After which time methanol was removed and the residue was diluted with water. The solution was adjusted to pH 9.0 to deposit N-benzyloxycarbonyl pradimicin A (2.2 g) as a red solid.

EXAMPLE 1

Preparation Of D-alanyl Pradimicin A (II,
$R^1=R^3=CH_3$; $R^2=NHCH(CH_3)CO_2H$; $R^4=H$;
$R^5=\beta$-D-xylosyl)

A suspension of D-alanine benzyl ester tosylate (116 mg) and triethylamine (46 μl) in tetrahydrofuran (2 ml) was mixed with a solution of N-Cbz pradimicin A (300 mg), N-hydroxybenzotriazole (49 mg) and dicyclohexylcarbodiimide (68 mg) in tetrahydrofuran (20 ml). After the mixture had been stirred for 2 hrs at 0° C. and then 13 hrs at room temperature, it was diluted with water (100 ml) and extracted with ethyl acetate (100 ml). The organic solvent was evaporated to give a solid residue which was dissolved in a mixture of methanol (30 ml), ethanol (10 ml) and water (20 ml), and hydrogenated in the presence of 5% palladium on carbon for 15 hours. The catalyst was filtered off and the filtrate was concentrated and applied on a reversed-phase silica gel column (Φ 2.2×45 cm). Elution was carried out with acetonitrile—0.15% $KH_2PO_4$ (21:79, pH 3.5) and fractions containing the homogenous product were pooled, concentrated and desalted by HP-20 chromatography (acetone-1N HCl, pH 3) to yield D-alanyl pradimicin A.HCl (27 mg). The hydrochloride salt was dissolved in water and the solution adjusted to pH 5.5 to provide D-alanyl pradimicin A (20 mg).

MP 213°–221° C. (Dec.).
IR (KBr) 3400, 1620, 1445, 1260 $cm^{-1}$.
UV $\lambda_{max}$ (50% methanol) nm ($\epsilon$) 221 (26,200) 276 (22,400), 502 (10,400).
SI-MS m/z 912 $(M+H)^+$.

EXAMPLE 2

Preparation of Pradimicin A Dimethylamide (II,
$R^1=R^3=CH_3$; $R^2=N(CH_3)_2$; $R^4=H$;
$R^5=\beta$-D-xylosyl)

A mixture of N-CBZ pradimicin A(224 mg, 0.23 mmol), N-hydroxysuccinimide (32 mg, 0.28 mmol) and dicyclohexylcarbodiimide ( 58 mg, 0.28 mmol) in tetrahydrofuran (5 ml) was stirred for 1 hr at room temperature and the resulting precipitate was filtered off. The filtrate was added to a 50% aqueous solution of dimethylamine (0.04 ml, 0.4 mmol) and the mixture was stirred at room temperature overnight and then concentrated in vacuo. The residue was chromatographed on a silica gel column (5 g, chloroform/methanol=10/1) to yield 215 mg (93%) of N-benzyloxycarbonyl pradimicin A dimethylamide.

MP: 130°–140° C.
IR $\nu_{max}$ (KBr) $cm^{-1}$: 1712, 1623.
UV $\lambda_{max}$ (MeOH) nm ($E_{1cm}^{1\%}$): 286 (203), 482 (79).
$^1$H NMR (400 MHz, DMSO-$d_6$+$D_2O$) δ: 1.01 (3H, d, J=5.6 Hz, 5'-$CH_3$), 1.25 (3H, d, J=6.9 Hz, CHCH_3), 2.59 (3H, s, 4'-N-$CH_3$), 2.87 & 3.10 (3H, each, s, N($CH_3$)$_2$), 4.89 (1H, q, J=6.9 Hz, CHCH_3).

A mixture of N-benzyloxycarbonyl pradimicin A dimethylamide (100 mg, 0.1 mmol), methanol (6 ml), water (1.5 ml) and acetic acid (1.5 ml) was stirred with 10% Pd-C (30 mg) under hydrogen atmosphere overnight. The solid was filtered off and the filtrate was concentrated in vacuo. The residue was dissolved in a small volume of 0.1N HCl and charged on a reversed phase column (25 mm×150 mm), eluted with water, and then successively with 20%, 30% and 40% aqueous acetonitrile. The desired fractions eluted with 40% aqueous acetonitrile were combined, concentrated to a small volume and lyophilized to yield 53 mg (61%) of a dark violet powder.

MP: >230° C. (grad. dec.).

IR $\nu_{max}$ (KBr) cm$^{-1}$: 1628.

UV $\lambda_{max}$(0.01N NaOH) nm ($E_{1cm}^{1\%}$): 319 (167), 496 (157).

$^1$H NMR (400 MHz, DMSO-d$_6$+D$_2$O) δ: 1.25 (2×3H, d, J=6.9 Hz, 5'-CH$_3$ and CHCH$_3$), 2.25 (3H, s, 3-CH$_3$), 2.86 & 3.11 (3H each, s, N(CH$_3$)$_2$), 3.91 (3H, s, 11-OCH$_3$), 4.91 (1H, q, J=6.9 Hz, CHCH$_3$), 6.71 (1H, d, J=2.6 Hz, 10-H), 6.84 (1H, br-s, 4-H), 7.12 (1H, d, J=2.6 Hz, 12-H), 7.62 (1H, br-s, 7-H).

Anal Calcd for C$_{42}$H$_{49}$N$_3$O$_{17}$.3H$_2$O: C 54.72, H 6.01, N 4.56. Found: C 54.54, H 5.63, N 4.72.

EXAMPLE 3

Preparation Of Pradimicin A Hydrazide (II, R$^1$=R$^3$=CH$_3$; R$^2$=NHNH$_2$; R$^4$=H; R$^5$=β-D-xylosyl)

A mixture of pradimicin A (210 mg, 0.25 mmol), dicyclohexylcarbodiimide (60 mg, 0.3 mmol) and N-hydroxysuccinimide (30 mg, 0.3 mmol) in dimethylformamide (4 ml) was stirred at room temperature for 1.5 hr and then filtered. The filtrate was stirred with hydrazine hydrate (13 mg, 0.3 mmol) at room temperature overnight and then subjected to reversed phase column chromatography. The column was washed with water and then eluted successively with 20%, 30% and 40% aqueous acetonitrile. The desired fractions eluted with 30% and 40% aqueous acetonitrile were combined and further purified by preparative HPLC (25% acetonitrile) to yield 9 mg (4%) of the title compound.

MP: >220° C. (grad. dec.)

IR $\nu_{max}$ (KBr) cm$^{-1}$: 1626, 1557.

UV $\lambda_{max}$(0.01N NaOH) nm ($E_{1cm}^{1\%}$): 319 (142), 496 (129).

$^1$H NMR (400 MHz, DMSO-d$_6$) δ: 1.15 (3H, d, J=6.8 Hz, 6'-CH$_3$), 1.30 (3H, d, J=7.3 Hz, CHCH$_3$), 2.20 (3H, s, 3-CH$_3$), 2.43 (3H, s, N—CH$_3$), 3.91 (3H, s, OCH$_3$), 4.35-4.42 (2H, m), 4.48 (1H, d, J=9.4 Hz, 1''-H), 4.60 (1H, d, J=6.8 Hz, 1'-H), 6.71 (1H, d, J=2.1 Hz, 10-H), 6.86 (1H, s, 4-H), 7.12 (1H, d, J=2.6 Hz, 12-H), 7.70 (1H, s, 7-H).

EXAMPLE 4

Preparation Of Pradimicin A Amide (II, R$^1$=R$^3$=CH$_3$; R$^2$=NH$_2$; R$^4$=H; R$^5$=β-D-xylosyl)

A methanol solution (2 ml) of pradimicin A methyl ester-HCl (95 mg) was added dropwise to a stirred solution of 28% ammonia (25 ml) and stirring was continued for 4 hours at room temperature. The solution was evaporated and the solid residue was treated with 0.25N NaOH in aqueous methanol (30 ml) at room temperature for 4 hours. The solution was then acidified to pH 3.5, concentrated and desalted by HP-20 column chromatography (100 ml) to yield semi-pure amide HCl (105 mg). The solid (100 mg) was applied on a column of reversed phase silica gel (φ20×450 mm). Elution was carried out with a mixture of CH$_3$CN-0.15% KH$_2$PO$_4$, pH 3.5 (21:79). The fractions containing homogenous BU-3608 amide were pooled, concentrated and desalted by HP-20 chromatography (100 ml, eluent:acetone-1N HCl, pH 3) to yield pure amide HCl (59 mg). An aqueous solution of the hydrochloride was adjusted to pH 6.0 to deposit the free form of pradimicin A amide (50 mg).

MP: 205°-208° C. (dec.).

IR (KBr)cm$^{-1}$ 3400, 1675, 1440, 1250.

UV $\lambda_{max}$ (0.01N NaOH - 50% MeOH) nm (ε) 245 (30,100), 320 (13,000), 496 (11,800).

SI-MS m/z 840 (M+H)$^+$.

EXAMPLE 5

Preparation Of Pradimicin A Methylamide (II, R$^1$=R$^3$=CH$_3$; R$^2$=NHCH$_3$; R$^4$=H; R$^5$=β-D-xylosyl)

The title compound (117 mg) was prepared according to the general procedure described in Example 4 using as starting materials pradimicin A methyl ester HCl (160 mg) and 40% aqueous methylamine (15 ml).

MP: 202°-205° C. (dec).

IR (KBr) cm$^{-1}$ 3400, 1620, 1440, 1290.

UV $\lambda_{max}$ (0.01N NaOH - 50% MeOH) nm (ε) 245 (30,600), 320 (13,500), 496 (12,300).

SI-MS; m/z 854 (M+H)$^+$.

EXAMPLE 6

Preparation Of Pradimicin A Butylamide (II, R$^1$=R$^3$=CH$_3$; R$^2$=NH(CH$_2$)$_3$CH$_3$; R$^4$=H; R$^5$=β-D-xylosyl)

The title compound (62 mg) was prepared according to the general procedure described in Example 4 using as starting materials pradimicin A methyl ester HCl (135 mg) and butylamine (10 ml).

MP: 200°-205° C. (dec.).

IR (KBr) cm$^{-1}$ 3400, 1625, 1600, 1440, 1255.

UV $\lambda_{max}$ (0.01N NaOH - 50% MeOH) nm (ε) 245 (31,600), 320 (13,300), 496 (12,400).

SI-MS m/z 898 (M+3H)$^+$.

EXAMPLE 7

Preparation of Glycyl Pradimicin A (II, R$^1$=R$^3$=CH$_3$; R$^2$=NHCH$_2$CO$_2$H; R$^4$=H; R$^5$=β-D-xylosyl)

A mixture of N-Cbz pradimicin A (107 mg, 0.11 mmol), N-hydroxysuccinimide (17 mg, 0.15 mmol) and DCC (31 mg, 0.15 mmol) in THF (2 ml) was stirred at room temperature for 1.5 hr. The reaction mixture was filtered and to the filtrate was added a mixture of glycine ethyl ester hydrochloride (21 mg, 0.15 mmol) and triethylamine (21 μl, 0.15 mmol) in THF (0.5 ml). The mixture was stirred at room temperature overnight and then diluted with ethyl acetate, washed succesively with dil. HCl and water, dried over MgSO$_4$ and concentrated in vacuo. The residue was chromatographed on a silica gel column (5 g) and eluted with 10% CH$_3$OH-CHCl$_3$ to yield 118 mg of the protected dipeptide of pradimicin A, which was dissolved in a mixture of EtOH (10 ml), MeOH (20 ml), water (5 ml) and acetic acid (1 ml) and hydrogenated in the presence of 10% Pd-C (30 mg) at room temperature overnight. The mixture was filtered and the filtrate was concentrated in vacuo. The residue was chromatographed on a C-18 column, which was washed with water and eluted with 50% CH$_3$CN. Fractions containing the desired product were combined, concentrated and lyophilized to yield 18 mg of glycyl pradimicin A ethyl ester. The ethyl ester was hydrolysed in a mixture of MeOH (3 ml) and 1N NaOH (3 ml) at room temperature for 2 hr. The mixture was concentrated to remove MeOH and subjected to C-18 column chromatography (elution, water and 30% CH$_3$CN) to give 9.5 mg (Y. 11%) of the title compound.

MP: >195° C. (grad. dec.).

IR $\nu_{max}$(KBr) cm$^{-1}$ 3366 (broad, 1733, 1607, 1558.

$^1$H NMR (DMSO-d$_6$) $\delta$1.28 (3H, d, J=6.4 Hz, 5'-CH$_3$), 1.31 (3H, d, J=7.3 Hz, 17-CH$_3$), 2.29 (3H, s, 3-CH$_3$), 3.83 (2H, d-AB$_q$, J=5.6 & 17 Hz, NHCH$_2$—COOH), 3.97 (3H, s, OCH$_3$), 6.97 (1H, d, J=2.6 Hz, 10-H), 7.16 (1H, s, 4-H), 7.32 (1H, d, J=2.6 Hz, 12-H), 8.05 (1H, S, 7-H), 8.20 (1H, t, J=5.6 Hz, NH-CH$_2$CO$_2$H, disappeared in D$_2$O.

What is claimed is:

1. A compound having the formula

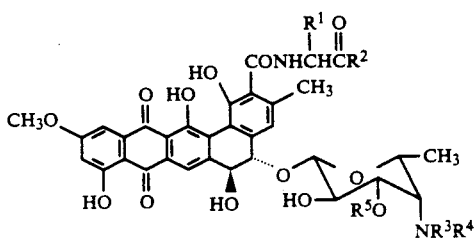

wherein

R$^1$ is selected from the group consisting of H, methyl and hydroxymethyl; when R$^1$ is methyl or hydroxymethyl the resulting amino acid has the D-configuration;

R$^2$ is selected from the group consisting of —NR$^6$R$^7$, —NHNR$^6$R$^7$, —NHCH$_2$CO$_2$H and (D)—NHCH(CH$_3$)CO$_2$H;

R$^6$ is H and R$^7$ is selected from the group consisting of H, C$_{1-6}$alkyl, C$_{3-6}$cycloalkyl, C$_{6-10}$aryl, and C$_{7-15}$aralkyl; or R$^6$ and R$^7$ are independently C$_{1-6}$alkyl; or R$^6$, R$^7$ and the nitrogen to which they are attached form a ring selected from the group consisting of pyrrolidine and piperidine.

R$^3$ and R$^4$ are each independently selected from the group consisting of H and C$_{1-6}$alkyl; and R$^5$ is H or $\beta$-D-xylosyl; or a pharmaceutically acceptable salt thereof.

2. A compound of claim 1 wherein R$^2$ is selected from the group consisting of amino, C$_{1-4}$alkylamino, di(C$_{1-4}$)alkylamino, hydrazino, —NHCH$_2$CO$_2$H and (D)—NHCH(CH$_3$)CO$_2$H.

3. A compound of claim 1 wherein R$^1$ is methyl.

4. A compound of claim 3 wherein R$^5$ is $\beta$-D-xylosyl.

5. A compound of claim 4 wherein R$^3$ is H and R$^4$ is methyl.

6. A compound of claim 5 wherein R$^2$ is amino.

7. A compound of claim 5 wherein R$^2$ is methylamino.

8. A compound of claim 5 wherein R$^2$ is dimethylamino.

9. A compound of claim 5 wherein R$^2$ is butylamino.

10. A compound of claim 5 wherein R$^2$ is hydrazino.

11. A compound of claim 5 wherein R$^2$ is (D)—NHCH(CH$_3$)CO$_2$H.

12. A compound of claim 5 wherein R$^2$ is —NHCH$_2$CO$_2$H.

13. A pharmaceutical composition which comprises an antifungal effective amount of a compound of claim 1 and a pharmaceutically acceptable carrier.

14. A method for treating fungal infections in a mammalian host which comprises administering to said host an antifungal effective dose of a compound of claim 1.

* * * * *